United States Patent
Danzer et al.

(10) Patent No.: US 10,890,673 B2
(45) Date of Patent: Jan. 12, 2021

(54) X-RAY DETECTOR HAVING A CARRIER ELEMENT WITH PROTECTIVE ELEMENT ALONG THE SIDE FACES

(71) Applicant: Siemens Healthcare GmbH, Erlangen (DE)

(72) Inventors: Ludwig Danzer, Wendelstein (DE); Harald Geyer, Bubenreuth (DE); Jan Wrege, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 142 days.

(21) Appl. No.: 16/135,048

(22) Filed: Sep. 19, 2018

(65) Prior Publication Data
US 2019/0090825 A1  Mar. 28, 2019

(30) Foreign Application Priority Data

Sep. 28, 2017  (DE) .................. 10 2017 217 327

(51) Int. Cl.
*G01T 1/24* (2006.01)
*G01T 1/20* (2006.01)
(Continued)

(52) U.S. Cl.
CPC ............ *G01T 1/244* (2013.01); *G01T 1/2018* (2013.01); *H01L 27/14659* (2013.01); *A61B 6/032* (2013.01); *A61B 6/4233* (2013.01)

(58) Field of Classification Search
CPC ....... A61B 6/035; A61B 6/032; A61B 6/4233; A61B 6/42; G01T 1/244; G01T 1/2018; H01L 27/14659
See application file for complete search history.

(56) References Cited

U.S. PATENT DOCUMENTS 6,495,836 B1  12/2002  Hata
2003/0218120 A1*  11/2003  Shibayama ......... H01L 27/1464
250/214.1
(Continued)

FOREIGN PATENT DOCUMENTS

DE  102014211602 A1  12/2015
DE  102014213734 A1  2/2016
(Continued)

OTHER PUBLICATIONS

Harald Geyer et al. "Rigid circuit board design for optically segmented sensor surfaces for underfilling smaller substrate dimensions". Siemens AG. 2015.
(Continued)

*Primary Examiner* — Chih-Cheng Kao
(74) *Attorney, Agent, or Firm* — Harness, Dickey & Pierce, P.L.C.

(57) ABSTRACT

An X-ray detector, including a stacking arrangement, includes an evaluation unit and a carrier unit. The evaluation unit and the carrier unit are electrically conductively connected via a plurality of connecting elements. An interspace is formed between the evaluation unit, the carrier unit and the plurality of connecting elements. A protective element is formed on side faces of the carrier unit, arranged essentially parallel to a stacking direction of the stacking arrangement. The protective element is formed in at least one section of the side faces along the entire outer circumference and along the edges of the side faces, facing the evaluation unit.

16 Claims, 10 Drawing Sheets

(51) Int. Cl.
*H01L 27/146* (2006.01)
*A61B 6/03* (2006.01)
*A61B 6/00* (2006.01)

(56) References Cited

U.S. PATENT DOCUMENTS

| | | | |
|---|---|---|---|
| 2015/0362603 A1* | 12/2015 | Ellwood | G01T 1/243 |
| | | | 250/370.08 |
| 2016/0015339 A1 | 1/2016 | Danzer et al. | |
| 2016/0116610 A1 | 4/2016 | Labayen de Inza et al. | |
| 2016/0170032 A1* | 6/2016 | Danzer | H01L 31/0203 |
| | | | 250/370.09 |
| 2017/0307766 A1* | 10/2017 | Abenaim | G01T 1/244 |

FOREIGN PATENT DOCUMENTS

| | | |
|---|---|---|
| DE | 102014221829 A1 | 4/2016 |
| DE | 102014225396 B3 | 4/2016 |
| EP | 1492168 A1 | 12/2004 |
| WO | WO 2016064374 A1 | 4/2016 |

OTHER PUBLICATIONS

German Office Action #102017217327.0 dated Jun. 5, 2018.

* cited by examiner

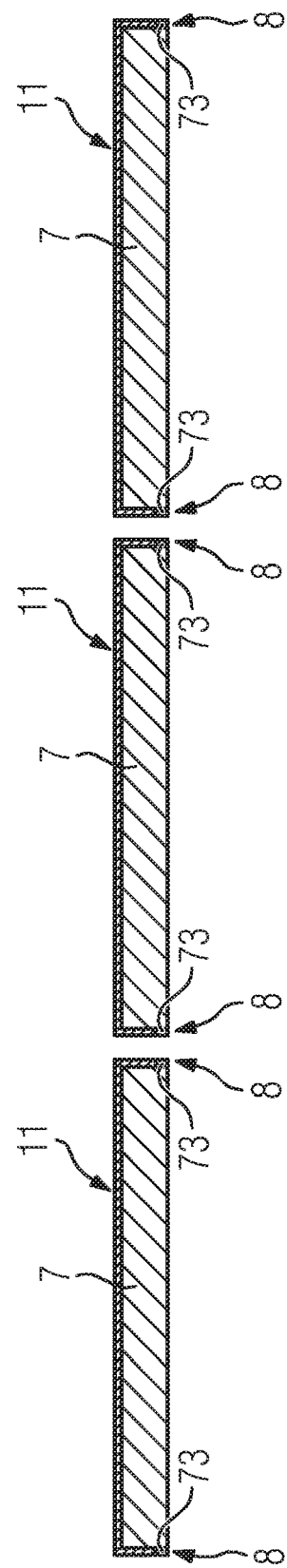
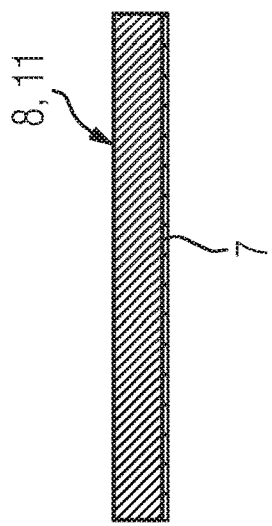

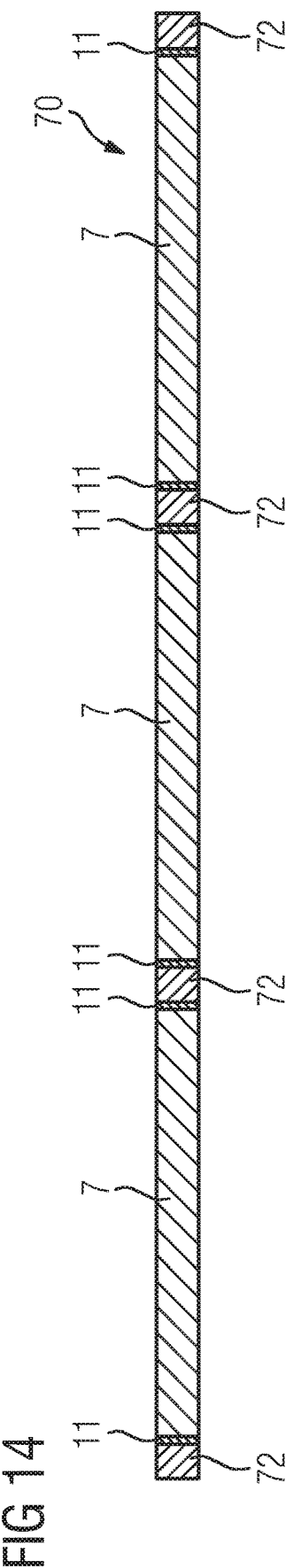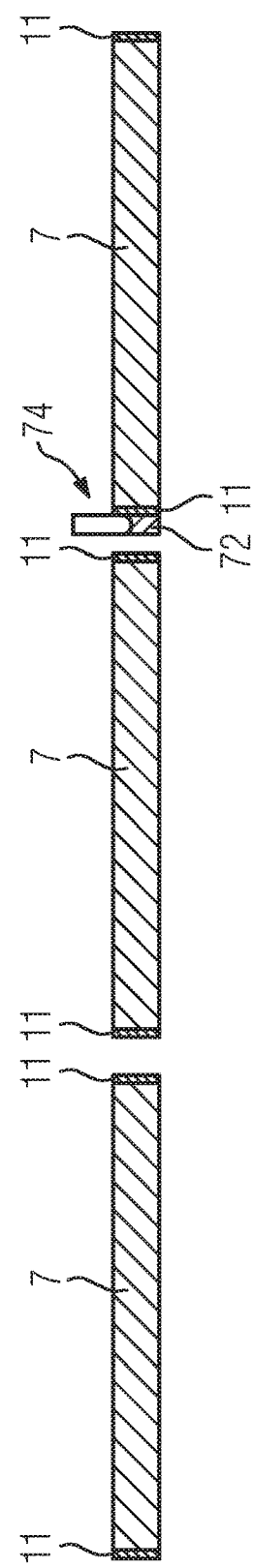

US 10,890,673 B2

X-RAY DETECTOR HAVING A CARRIER ELEMENT WITH PROTECTIVE ELEMENT ALONG THE SIDE FACES

PRIORITY STATEMENT

The present application hereby claims priority under 35 U.S.C. § 119 to German patent application number DE 102017217327.0 filed Sep. 28, 2017, the entire contents of which are hereby incorporated herein by reference.

FIELD

Embodiments of the invention generally relate to an X-ray detector, to a medical device and to a method for producing the X-ray detector, wherein the side faces of a carrier element incorporated by the X-ray detector are formed by way of a protective element in such a way that penetration of a underfill material is prevented.

BACKGROUND

Counting direct-conversion X-ray detectors or integrating indirect-conversion X-ray detectors can be used in X-ray imaging, for example in computerized tomography, angiography or radiography.

In direct-conversion X-ray detectors the X-ray radiation or the photons can be converted by way of a suitable converter material into electrical pulses. For example CdTe, CZT, CdZnTeSe, CdTeSe, CdMnTe, InP, $TlBr_2$, $HgI_2$, GaAs or others can be used as the converter material. The electrical pulses are evaluated by an electronic evaluation device, for example an integrated circuit (Application Specific Integrated Circuit, ASIC). In counting X-ray detectors, incident X-ray radiation is measured by counting the electrical pulses which are triggered by the absorption of X-ray photons in the converter material. The level of the electrical pulse is, as a rule, proportional to the energy of the absorbed X-ray photon. As a result, a spectral item of information can be extracted by comparison of the level of the electrical pulse with a threshold value.

In indirect-conversion X-ray detectors the X-ray radiation or the photons can be converted by way of a suitable converter material into light and via photodiodes into electrical pulses. Scintillators, for example GOS ($Gd_2O_2S$), CsJ, YGO or LuTAG, are frequently used as the converter material. Scintillators are used in particular in medical X-ray imaging in the energy range up to 1 MeV. What are known as indirect-conversion X-ray detectors, what are known as scintillator detectors are conventionally used in which the X-ray or gamma radiation is converted into electrical signals in two stages. In a first stage the X-ray or gamma quanta are absorbed in a scintillator element and converted into optically visible light. This effect is called luminescence. The light excited by luminescence is then converted in a second stage by a first photodiode optically coupled to the scintillator element into an electrical signal, read out via an electronic evaluation device or electronic readout device and then forwarded to an arithmetic unit.

From document DE 10 2014 213 734 A1 an imaging device is known for electromagnetic radiation, in particular for X-ray and/or gamma radiation, which comprises a lamination comprising a number of detection elements, a number of readout circuit boards and a base circuit board, wherein the or each detection element is electrically contacted in each case by a readout circuit board by way of plurality of first solder contacts, with the or each readout circuit board having a plurality of through-connections, and with the or each readout circuit board being electrically contacted by the base circuit board by way of a plurality of second solder contacts.

From document DE 10 2014 221 829 A1 a method is known for producing a sensor board for a detector module, wherein a plurality of readout units is provided, wherein the readout units are positioned in a stacked construction in each case on a shared sensor layer, and wherein, once all readout units have been positioned, they are jointly fixed to the sensor layer, forming a hybrid.

From document DE 10 2014 225 396 B3 a sensor board is known for a detector module, comprising in a stacked construction at least one readout unit and a sensor layer arranged in the stacking direction at a distance from the readout unit, wherein the sensor layer, in a longitudinal direction transverse to the stacking direction, has, in at least one edge region, an overhang with respect to the readout unit, wherein the interspace present due to the spacing between the sensor layer and the readout unit is filled with a cured fill material in such a way that at least one edge region of the sensor layer is free from the fill material.

From the publication "Starrleiterplattendesign für optischsegementierte Sensorflächen zur Unterfüllung bei kleineren Substratabmaßen" [Rigid circuit board design for optically segmented sensor surfaces for underfilling smaller substrate dimensions], Prior Art Journal 2015 #23 dated Nov. 20, 2015, DOI: 10.18169/PAPDEOTT004794, it is known that, due to the formation of an overhang as early as during production of the circuit board, which is subsequently located below the protruding component or the protruding components, underfilling can take place without turning the flat module. The shape of the overhang is determined here by the upper circuit board layers—in the case of multi-layer circuit boards. The individual circuit boards can be fitted and underfilled in the panel. Separation takes place only after curing of the underfill material. However, it is also possible to separate the panel first and then fit the individual circuit boards and underfill them. The inventors have recognized one drawback of this method as being that the dimensions of a surface of an evaluation unit facing the incident X-ray radiation and a surface of the circuit board or the carrier unit remote from the incident X-ray radiation are different in a stacked construction.

Previously, ceramic substrates, for example LTCC or HTCC, have been used as the material for the carrier unit in order to satisfy the requirements of the distortion and warping of the evaluation unit connected to the carrier unit, in particular an X-ray detector for a computerized tomography system. To ensure higher stability during operation, in particular during rotation inside the gantry, an underfill can be formed between the carrier unit and the evaluation unit. The underfill can form a planar connection between the evaluation unit and the carrier unit and prevent the formation of defects in the electrically conductive connections between the evaluation unit and the carrier unit, in particular what is known as a ball tear, during operation.

The underfill is formed in such a way that the underfill material is laterally provided via a pipette at the gap resulting between evaluation unit and carrier unit. The underfill material penetrates by way of capillary force into the interspace between evaluation unit and carrier unit. The underfill material is not wetted at the side faces of the carrier unit when ceramic substrates, for example LTCC or HTCC, are used. Similarly, the underfill material does not penetrate into the individual layers of the ceramic substrate.

SUMMARY

The inventors have recognized that it is a problem that when using an organic substrate or a multi-layer circuit board instead of a ceramic substrate, wetting of the underfill material at the side faces of the carrier unit and penetration of the underfill material into the individual layers of the carrier unit occur.

During the production of circuit boards, which are manufactured in the panel, it is necessary to separate them from the panel after production. For this purpose, the individual layers are usually separated via a milling cutter. Since the individual layers of a circuit board or a panel are composed of a polymer-glass fabric matrix, they are exposed at the sides of the individual circuit boards during separation.

During underfilling, wetting accordingly occurs at the side faces or edges since the laminate structure is not closed at the side face of the circuit board. The result of this is that, firstly, the underfill material penetrates into the substrate along the glass fibers, and secondly, wetting at the side leads to displacement of the underfill material onto tools that are being used, for example a frame or a holding device.

The inventors have recognized that cleaning the carrier unit in the uncured state of the underfill material but without removing the underfill material from the interspace to be underfilled is very difficult or barely possible.

Embodiments of the invention disclose an X-ray detector, a medical device and a method for producing the X-ray detector which enables use of a multi-layer circuit board as the carrier unit in conjunction with an underfill of the interspace.

Embodiments of the invention are directed to an X-ray detector, a medical device and a method for producing the X-ray detector.

At least one embodiment of the invention relates to an X-ray detector having a stacking arrangement with an evaluation unit and a carrier unit, wherein the evaluation unit and the carrier unit are electrically conductively connected via a plurality of connecting elements. An interspace is formed between the evaluation unit, the carrier unit and the plurality of connecting elements. A protective element is formed on side faces of the carrier unit arranged essentially parallel to the stacking direction, wherein the protective element is formed in at least one section of the side faces along the entire outer circumference and along the edges of the side faces facing the evaluation unit.

At least one embodiment of the invention also relates to a medical device having an embodiment of the inventive X-ray detector. According to one embodiment of the invention, the medical device is a computerized tomography system. The advantages of the embodiments of the inventive X-ray detector can be transferred to the medical device, in particular the computerized tomography system. Distortion or warping of the evaluation unit can advantageously be reduced or prevented. The medical device can advantageously be more inexpensively produced. An extended life of the X-ray detector can advantageously lead to lower maintenance costs.

At least one embodiment of the invention also relates to a method for producing an X-ray detector comprising: providing, generating, forming, separating and connecting. During the providing, the carrier unit is provided in a panel. During the generating, side faces are generated along the outer circumference of the carrier unit, with the carrier unit remaining in the panel. During the forming, the protective element is formed on side faces of the carrier unit arranged essentially parallel to the stacking direction, wherein the protective element is formed in at least one section along the entire outer circumference and along the edges of the side faces facing the evaluation unit. During the separating, the carrier unit with the formed protective element is separated from the panel. During the connecting, the carrier unit and the evaluation unit are connected via a plurality of connecting elements and the interspace is formed in the process. The method can, in s particular example embodiment, be carried out in the following order: providing, generating, forming, separating and connecting.

BRIEF DESCRIPTION OF THE DRAWINGS

Example embodiments of the invention will be illustrated in more detail below with reference to drawings, in which:

FIG. 7 schematically shows in a cross-section a concept of the carrier units separated from an inventive panel according to a first embodiment;

FIG. 8 schematically shows in a side view a concept of the carrier units separated from an inventive panel according to a first embodiment;

FIG. 14 schematically shows a concept of an inventive panel according to a fourth embodiment in a first production step;

FIG. 15 schematically shows in a cross-section a concept of the carrier units separated from an inventive panel according to a fourth embodiment;

DETAILED DESCRIPTION OF THE EXAMPLE EMBODIMENTS

Figure 1:
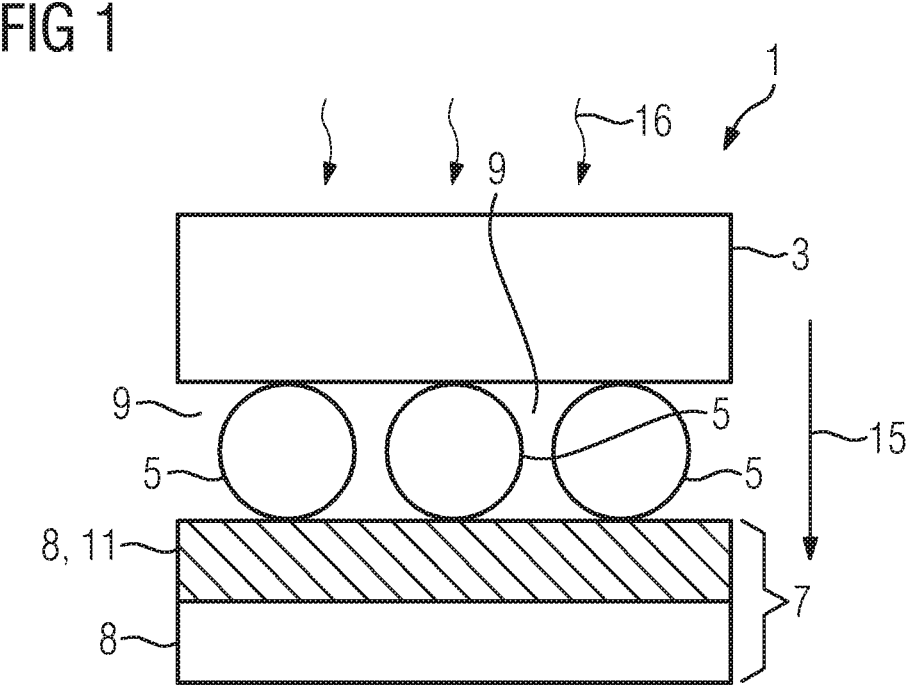
FIG. 1 schematically shows a concept of an inventive X-ray detector according to a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray detector having a stacking arrangement with an evaluation unit and a carrier unit, wherein the evaluation unit and the carrier unit are electrically conductively connected via a plurality of connecting elements. An interspace is formed between the evaluation unit, the carrier unit and the plurality of connecting elements. A protective element is formed on side faces of the carrier unit arranged essentially parallel to the stacking direction, wherein the protective element is formed in at least one section of the side faces along the entire outer circumference and along the edges of the side faces facing the evaluation unit.

The carrier unit be designed as a stabilizing unit or connecting unit for receiving a plurality of evaluation units. A plurality of evaluation units can be associated with one carrier unit. The carrier unit can be formed as an intermediate unit, in particular as what is known as an interposer, wherein the carrier unit is associated with one evaluation unit or a plurality of evaluation units. The connecting elements can be arranged in the interspace. The interspace can comprise the gaps between the connecting elements. The interspace can in particular comprise the volume between the carrier unit and the evaluation unit, with the connecting elements being excluded from the volume of the interspace.

The protective element can be formed as a(n) (edge) coating. The protective element can in particular comprise a solder resist and/or at least one section of a through-connection. The protective element can be configured in such a way that wetting of the underfill material and penetration of the underfill material are prevented.

The stacking direction can be oriented essentially parallel to the incident direction of the X-ray radiation. Compared to the carrier unit, the evaluation unit can be arranged closer to the X-ray radiation source. The carrier unit can be formed in particular in the shape of a cube. The carrier unit can in particular have side faces which extend essentially parallel to the stacking direction. Four side faces can be arranged along the outer circumference of the carrier unit. The side faces can enclose the entire outer circumference. The protective element is preferably formed along the entire outer circumference on the side faces, with at least one section of the side faces being covered by the protective element. The section extends as a cohesive region along the entire outer circumference. The protective element extends along the at least partial height of the carrier unit beginning at the edge between the side face and the surface of the carrier unit facing the X-ray radiation or the interspace. The protective element extends from this edge along the stacking direction at least in one section. The section comprises this edge. The section can partially comprise the side face along the height. The section can completely comprise the side face. The protective element preferably forms a closed surface.

Wetting or penetration of possible underfill material into the carrier unit can advantageously be reduced or prevented. Damage caused by the penetration of possible underfill material can advantageously be avoided. The X-ray detector can advantageously be produced more inexpensively. Warping of the evaluation unit(s) can advantageously be avoided equally as well or better than in known solutions.

According to one embodiment of the invention, the X-ray detector also has an underfill of the interspace with an underfill material. The underfill can essentially fill the entire volume of the interspace. The underfill can essentially completely fill the interspace. The boundary faces parallel to the side faces can be concave, plane or in particular convex.

The underfill has an underfill material. The underfill material has in particular a fill material. The fill material can have an epoxide compound, a plastics material, a composite material or a (pre)polymer. The fill material can have a binder material. A matrix can be formed from a binder material and filler. The fill material can in particular have an epoxy resin. At the instant of filling of the underfill between evaluation unit and carrier unit, the material of the underfill, for example having an epoxide compound, an epoxy resin or a prepolymer, can be liquid or free-flowing. The underfill can advantageously cure, for example under the effect of temperature.

The underfill or the underfill material can have a thermal conductivity of more than 0.5 W/mK, preferably more than 2 W/mK, particularly preferably more than 6 W/mK. The fill material or the underfill can preferably be electrically insulated or non-conductive. The fill material can have a filler. The filler can have a low, in particular thermal, coefficient of expansion. The filler can have for example $Al_2O_3$, $SiO_2$, BN, AlN, TiN, $TiO_2$, PZT ($PbZrTiO_3$), $ZrO_2$ or YSZ (what is known as yttria-stabilized zirconia). The filler can advantageously contribute to the mechanical stability of the stacked construction. The concentration of the filler can be chosen in such a way that the viscosity of the fill material, for example in the free-flowing state, is between 3,300 mPa·s and 6,5000 mPa·s. The diameter or the size of the filler particles of the filler can in particular be smaller than the distance between the evaluation unit and the carrier unit, for example smaller than 33 percent, preferably 20 percent and particularly preferably 10 percent of the distance. The filler can advantageously be adjusted to adjust the thermal coefficient of expansion to the adjacent units, the evaluation unit and the carrier unit. The form of the filler particles can be for example spherical, round, angled or flocculent. The thermal conductivity of the underfill can advantageously be increased by the purposeful use of fillers with high thermal conductivities, such as for example diamond, nanoparticles, graphenes or carbon nanotubes. The thermal coefficient of expansion of the underfill, the fill material or the binder material can be for example less than 100 ppm/K and in particular less than 50 ppm/K and preferably be in the range of 25 to 30 ppm/K. Increased stability of the X-ray detector can advantageously be achieved. Warping of adjacent evaluation units can advantageously be avoided or reduced. Improved dissipation of heat from the evaluation unit through to the carrier unit can advantageously be achieved.

According to one embodiment of the invention the protective element is impermeable to the underfill material. The protective element can have a solder resist. The protective element, in particular having a solder resist, can be used to protect the circuit board from corrosion or mechanical damage. The solder resist can comprise for example epoxy resin. The protective element can have a photostructurable solder resist (LPI, liquid photoimageable solder mask) or a non-photostructurable solder resist. The non-photostructurable solder resist can either be cured thermally or via UV-light. The non-photostructurable solder resist can be applied by screen printing methods using structured screens. The photostructurable solder resist can be present as a viscous liquid or photopolymer film. A photopolymer film can be applied by laminating. Following application the photostructurable solder resist can be dried, optionally exposed and optionally developed. The protective element can have a metallic material, in particular a metal. The protective element can exhibit for example copper.

Wetting or penetration of possible underfill material into the carrier unit can advantageously be reduced or prevented. Damage caused by the penetration of possible underfill material into the carrier unit can advantageously be prevented.

According to one embodiment of the invention, the protective element is formed as a coating. The section at the side faces of the carrier unit and/or the surface of the carrier unit facing the evaluation unit, in particular also with carrier units that have already been separated or isolated from the panel, can be coated by way of screen printing, spraying, dipping, curtain coating or roller application of a solder resist. The coating can in particular be formed in a section of the side faces of the carrier unit and optionally additionally at the surface of the carrier unit facing the evaluation unit. A closed surface of the protective element can advantageously be achieved.

According to one embodiment of the invention, the protective element is also formed on the surface of the carrier unit facing the evaluation unit. At the same time as the protective element is being formed in the section of the side faces, the protective element can advantageously be expanded on the surface of the carrier unit facing the evaluation unit, in particular with a solder resist. Penetration of the solder material of the connecting elements into the carrier unit can advantageously be avoided. The protective element can advantageously be implemented at the same time as a coating of the surface of the carrier unit.

According to one embodiment of the invention, the protective element is formed by sections of at least partially coated or partially filled adjoining holes parallel to the stacking direction. The at least partially coated or partially filled adjoining holes can be formed as through-connections, with these in particular not being used as an electrically conductive connection. The protective element can comprise at least sections of at least partially coated or partially filled adjoining holes. The sections of the holes can be configured in such a way that the holes have their complete height corresponding to the essentially entire height of the carrier unit or a partial height of the carrier unit parallel to the stacking direction, but the entire base area of, for example, cylindrical holes is not retained. A portion of the base area can be removed along the height of the holes by milling.

The protective element can comprise complete, at least partially coated or partially filled adjoining holes, so the entire base area of the, for example, cylindrical holes is retained. For example, a section of the empty layers of the panel can remain around the outer circumference of the protective element. The sections of the at least partially coated or partially filled adjoining holes or the complete, at least partially coated or partially filled adjoining holes form the protective element, with the protective element having a closed face at least in sections of the side faces, in particular along the entire side faces.

The at least partially coated or partially filled adjoining holes can be arranged in such a way that the base areas of adjacent holes overlap, for example by gradual formation and optionally partially slightly offset formation of adjacent holes. With gradual formation, for example a first set of holes can be drilled and at least partially filled. A second set of holes can then be drilled and be at least partially filled, so gaps between the holes of the first set are closed and a continuous protective element is formed. The protective element can advantageously be easily produced. A particularly stabile and impermeable protective element can advantageously be formed. The hole can be at least partially filled with a metallic material, for example copper, or with a solder resist. The at least partial filling of the hole can in particular comprise coating the circumferential surface of the hole along the entire height of the hole. The hole can preferably be completely filled.

According to one embodiment of the invention, the carrier unit is a multi-layer circuit board. The circuit board can be a carrier for electronic components. The circuit board can be used for mechanical fastening and electrical connection. The circuit board can comprise an electrically insulating material having conductive connections adhering thereto as tracks. Fiber-reinforced plastics material or a polymer-glass fabric matrix can be used as the insulating material. The circuit board can have a plurality of thinner circuit boards, with the plurality of thinner circuit boards being glued to each other by what are known as prepregs. This multi-layer circuit board, what is known as a multi-layer circuit board, can have for example up to 48 layers. The multi-layer circuit board can have for example 4 to 12 layers. The connections between the layers can be produced by through-connections. An increased packing density can advantageously be achieved in the circuit board. The circuit board can have an FR4 material and a laminate.

According to one embodiment of the invention, the evaluation unit has a photodiode or an integrated circuit. The evaluation unit can in particular comprise a photodiode, preferably a plurality of photodiodes, and/or an integrated circuit. The evaluation unit can comprise a plurality of detector elements or pixels. The evaluation unit can comprise a, for example direct-conversion or an indirect-conversion, converter element, with the converter element comprising the surface facing the X-ray radiation. The evaluation unit can be associated with a photodiode, preferably a plurality of photodiodes, and/or an integrated circuit, wherein the evaluation unit can be designed as an intermediate unit, in particular as what is known as an interposer. A stray radiation grid can be arranged on the surface of the converter element. A distortion and/or warping of the evaluation unit or the plurality of evaluation units can advantageously be reduced, in particular the distortion and/or warping of the evaluation unit can be less than 100 µm.

According to one embodiment of the invention, the plurality of connecting elements has a plurality of solder joints. The connecting element can be configured as a solder joint. The connecting element can comprise an electrically conductive connection from the evaluation unit to the carrier unit, for example for signal transmission and/or current or voltage supply. The connecting element can form a mechanical connection of the evaluation unit with the carrier unit. The solder joint can be designed as a solder ball, as what is known as a copper pillar or as what is known as a stud bump. A mechanical and at the same time electrically conductive connection can advantageously be formed between the evaluation unit and the carrier unit.

At least one embodiment of the invention also relates to a medical device having an embodiment of the inventive X-ray detector. According to one embodiment of the invention, the medical device is a computerized tomography system. The advantages of the embodiments of the inventive X-ray detector can be transferred to the medical device, in particular the computerized tomography system. Distortion or warping of the evaluation unit can advantageously be reduced or prevented. The medical device can advantageously be more inexpensively produced. An extended life of the X-ray detector can advantageously lead to lower maintenance costs.

At least one embodiment of the invention also relates to a method for producing an X-ray detector comprising: providing, generating, forming, separating and connecting. During the providing, the carrier unit is provided in a panel. During the generating, side faces are generated along the outer circumference of the carrier unit, with the carrier unit remaining in the panel. During the forming, the protective element is formed on side faces of the carrier unit arranged essentially parallel to the stacking direction, wherein the protective element is formed in at least one section along the entire outer circumference and along the edges of the side faces facing the evaluation unit. During the separating, the carrier unit with the formed protective element is separated from the panel. During the connecting, the carrier unit and the evaluation unit are connected via a plurality of connecting elements and the interspace is formed in the process. The method can, in s particular example embodiment, be carried out in the following order: providing, generating, forming, separating and connecting.

During the providing, the carrier unit is provided in the panel. During production, the panel can be structured or constructed in such a way that at least one carrier unit is formed in the panel. The individual layers of the panel can comprise, for example around the outer edges of the carrier unit or between adjacent carrier units, an empty layer or a connecting layer. The individual layers of the panel can comprise, for example around the outer edges of the carrier unit or between adjacent carrier units, an empty layer, a non-adhesive layer and a connecting layer.

During the generating, the side faces can be generated for example by partial milling along the outer edges of the carrier unit, in particular in order to remove the empty layer and the non-adhesive layer. During the generating, the side faces can be generated by way of holes along the outer edges of the carrier unit. The holes can occur for example in an empty layer or a connecting layer.

During the forming, the protective element is formed. The protective element is formed in particular on the side faces. The forming can include application of a solder resist or an at least partial filling of the holes.

The separating comprises in particular the complete separation of the carrier unit from the panel, wherein in particular, milling can be included.

During the connecting, the carrier unit is connected to the evaluation unit via connecting element. The connecting elements can have a solder material. Connecting can for example include what is known as reflow soldering.

The, in particular standardized, production of a carrier unit can occur predominantly in the panel. As a rule, a panel comprises a plurality of carrier units. During production of the panel or the carrier unit, the individual layers are connected and pressed together. During production, the layers are, as a rule, stacked one above the other over their complete surface. The inventors have recognized that lateral coating of the carrier unit in the panel has the advantage that, for example, subsequent wetting due to the underfill material can be prevented. If circuit boards are produced in this way then they can be liberated from the panel for separation. This occurs predominantly by milling (out) the individual circuit boards.

During the separating, the carrier unit is completely separated from the panel. For example, the partial connection via connecting layer or connecting web can be severed. For example, the separation can occur along the outer circumference of the protective element, for example formed by the at least partially coated or partially filled adjoining holes, wherein the separation can occur along the at least partially coated or partially filled adjoining holes or by way of the at least partially coated or partially filled adjoining holes. During the separating, complete separation can be carried out by milling. The separating can include a milling step.

The separating or the generating can include at least partial milling along the outer circumference of the carrier unit. The milling head diameter can be in the range of 0.8 mm-1.0 mm. The milling head diameter can be regarded as a limitation for the cavity width, in other words the distance between the carrier units in the panel or the width of the empty layers parallel to the distance of adjacent carrier units. A depth of for example 1 mm or a half thickness of the carrier unit can be separated with a milling head diameter in the range of 0.8 mm-1.0 mm.

Wetting or soiling of tools can advantageously be avoided. A protective element can advantageously be formed in at least one section of the side faces of the carrier element. An organic circuit board can advantageously be used as a substrate carrier or carrier unit for photodiodes or sensor elements or integrated circuits in X-ray detectors, with side by side mounting of a plurality of X-ray detectors, for example in a matrix, advantageously being possible.

According to one embodiment of the invention, the method also includes filling, with the interspace being filled with an underfill material. Increased stability of the X-ray detector can advantageously be achieved. Improved cooling of the evaluation unit can advantageously be enabled. The filling can advantageously be carried out via a pipette, with wetting and penetration of the underfill material into the carrier unit being avoided.

According to one embodiment of the invention, generating the side faces comprises milling along the outer circumference of the carrier unit. Before the forming the protective element, one side face of the carrier unit is generated in the generating. For example, after milling, a partial connection can remain between the individual carrier units or circuit boards in the panel, for example due to a connection existing after milling in the lower of the layers remote from the evaluation unit. Milling along the outer circumference can preferably not lead to complete separation of the carrier unit from the panel. An at least partial connection of the carrier unit can preferably remain in the panel.

The individual layers of the panel can comprise, for example around the outer edges of the carrier unit or between adjacent carrier units an empty layer, a non-adhesive layer and a connecting layer. Only the lower layers can be completely connected together via a connecting layer or a connecting web. For example copper is extensively separated or instead of the prepreg a non-adhesive film is inserted from the layer up to which the protective element should be formed. What is known as the release layer or the non-adhesive layer can be what is known as a no-flow prepreg which does not flow down during the pressing process of the individual layers of the circuit board or panel and is removed again for example after separation or during separation.

After production or provision of the panel, the side faces or the sections of the side faces can be generated from above or from the subsequent direction of incidence of X-ray radiation during the generating by milling. Just one connection on the underside can remain for example as a connecting layer or connecting web. In the case of a connecting web, a partial connection of the carrier unit remains in the panel, wherein at least one small web is formed for connecting the carrier unit in the panel in particular also during forming of the protective layer. In the case of a connecting layer, an in particular planar connection remains, in particular also during forming of the protective layer.

During the forming, a for example all-over coating of the panel can occur for example by way of solder resist, wherein the sections on the side faces as well as the surface subsequently facing the evaluation unit can be coated with the solder resist. Once a first milling process has already taken place from the upper side or the surface of the panel facing the evaluation unit during the generating, a coating on the sections of the side faces of the carrier unit can be achieved in the upper layer region during the forming or during coating with solder resist. The protective element can advantageously occur in the sections on the side faces of the carrier unit and on the surface facing the evaluation unit in the same step.

The protective element can be formed by way of spray coating or by way of a curtain coating process. With the curtain coating process a panel can be pushed on a conveyor belt through a solder resist curtain, so a protective element is formed on the carrier unit. The thickness of the protective element can vary along the height, wherein the protective element can be thicker in particular in the direction of the surface remote from the evaluation unit, in particular in the vicinity of the connecting layer or the connecting web. When UV-curing solder resist is used, a more uniform thickness of the protective element can advantageously be achieved along the height of the carrier unit.

The coating in the upper layer region or the protective element can advantageously prevent wetting of the underfill material on the side faces of the carrier unit during subsequent processing steps, for example during the filling. The protective element can advantageously the organic substrate or the carrier unit against penetration of the underfill material into the carrier unit, for example having a polymer-glass matrix, prevents in the section.

Alternatively, the protective layer of the carrier unit can be coated or formed after complete separation from the panel. For example, the carrier unit can be dipped in a solder resist basin. For example, the carrier unit can be coated by way of spray coating, for example as a selective coating.

The protective element can have a thickness in the region of 10 μm-20 μm. The extent of the protective element along the height of the carrier unit can be for example at least a third of the height, preferably at least half the height. Wetting of the open layers on the side faces of the carrier unit with the underfill material can advantageously be prevented. The protective element advantageously protects the carrier unit against penetration of the underfill material into the layers of the carrier unit. The carrier unit, in particular in the region of the pipette used for filling, can advantageously be protected by the protective element.

Preparation for generating the side faces can advantageously take place during construction or during production of the panel, for example by connecting layers, empty layers and non-adhesive layers being arranged in the region between adjacent carrier units. Selective coating of the carrier unit can advantageously be achieved which can advantageously be necessary as required in respect of signal routing or a current strength. The protective element can advantageously be inexpensively formed.

According to one embodiment of the invention, generating the side faces comprises drilling a plurality of holes along the outer circumference of the carrier unit. The hole can be formed along the entire height of the carrier element. The individual layers of the panel can comprise, for example around the outer edges of the carrier unit or between adjacent carrier units, an empty layer or a connecting layer.

The hole can be generated by mechanical drilling or else by using laser methods. The hole can be milled. The hole can be formed in particular in the region of the empty layer or the connecting layer. The hole, what is known as a blind via, can be formed in a section of the height of the carrier element, with the hole beginning at an edge of the side faces facing the evaluation unit. The hole runs essentially parallel to the stacking direction. The hole can have an essentially constant diameter along the height of the carrier unit. If the hole is formed in only one section of the height of the carrier element, then a connecting layer or a connecting web can remain, so firstly all holes can be formed along the outer circumference of the carrier unit and the holes can subsequently be at least partially filled.

The protective element can be produced in that the hole in the carrier element is seeded, for example faced with a catalyst, then catalytically metalized and thereafter is optionally electrolytically strengthened in order to form a thicker metal layer. The metalization, the metal layer and/or the filling of the hole can exhibit copper. The hole can be completely filled, for example with a metallic material or a solder resist or a material which fulfils the protective function of the protective element.

The holes can be formed around the entire outer circumference of the carrier unit. A narrow arrangement of the holes or overlapping of the holes can lead, after separation of the carrier units from the panel, to a closed protective element being formed at least in one section of the side faces of the carrier unit. The individual laminate layers can advantageously be protected by the protective element. The glass fiber structure of the fabric of the carrier unit can advantageously be limited by the protective element. The protective element can advantageously seal the carrier unit along the outer circumference. During filling, the underfill material advantageously cannot penetrate between the individual layers of the carrier unit. Wetting can advantageously be avoided. The surface facing the evaluation unit can be coated for example in the panel, for example before generation of the side faces or the drilling. The holes can be partially or completely metalized and/or be formed in the panel with solder resist as what are known as plugged vias. The protective element is formed along the outer circumference of the carrier unit. The protective element can have an undulating structure corresponding to the adjacent holes or have an essentially plane surface formed in particular by separating. The at least partially filled holes or section of the at least partially filled holes can form the outer limit of the carrier unit as a protective element.

Holes, for example also called through-connections or vias, can advantageously be arranged side by side very closely together or so as to overlap. The holes can in particular be cylindrical. The holes can be arranged essentially parallel to each other, wherein the axes of rotation of the holes run essentially parallel.

FIG. 1 shows an example embodiment of the inventive X-ray detector 1 according to a first embodiment. The X-ray detector 1 has a stacking arrangement with an evaluation unit 3 and a carrier unit 7. The evaluation unit 3 and the carrier unit 7 are electrically conductively connected via a plurality of connecting elements 5. An interspace 9 is formed between the evaluation unit 3, carrier unit 7 and plurality of connecting elements 5. A protective element 11 is formed on the side faces 8 of the carrier unit 7 arranged essentially parallel to the stacking direction 15, wherein the protective element 11 is formed in at least one section of the side faces 8 along the entire outer circumference and along the edges of the side faces 8 facing the evaluation unit 3. The X-ray detector 1 has an evaluation unit 3 and a carrier unit 7, which are mechanically and electrically conductively connected via connecting elements 5. Formed between the carrier unit 7 and evaluation unit 3 is an interspace 9. The carrier unit 7 has a side face 8. The protective element 11 is formed on side faces 8 of the carrier unit 7 arranged essentially parallel to the stacking direction 15, wherein the protective element 11 is formed in at least one section of the side faces 8 along the entire outer circumference and along the edges of the side faces 8 facing the evaluation unit 3.

The direction of incidence of the X-ray radiation 16 runs essentially parallel to the stacking direction 15 of the stacked construction. The evaluation unit 3 is arranged closer to the source of the X-ray radiation compared to the carrier unit 7. The protective element 11 is impermeable to the underfill material. The evaluation unit 3 has a photodiode or an integrated circuit. The plurality of connecting elements 5 has a plurality of solder joints.

Figure 2:
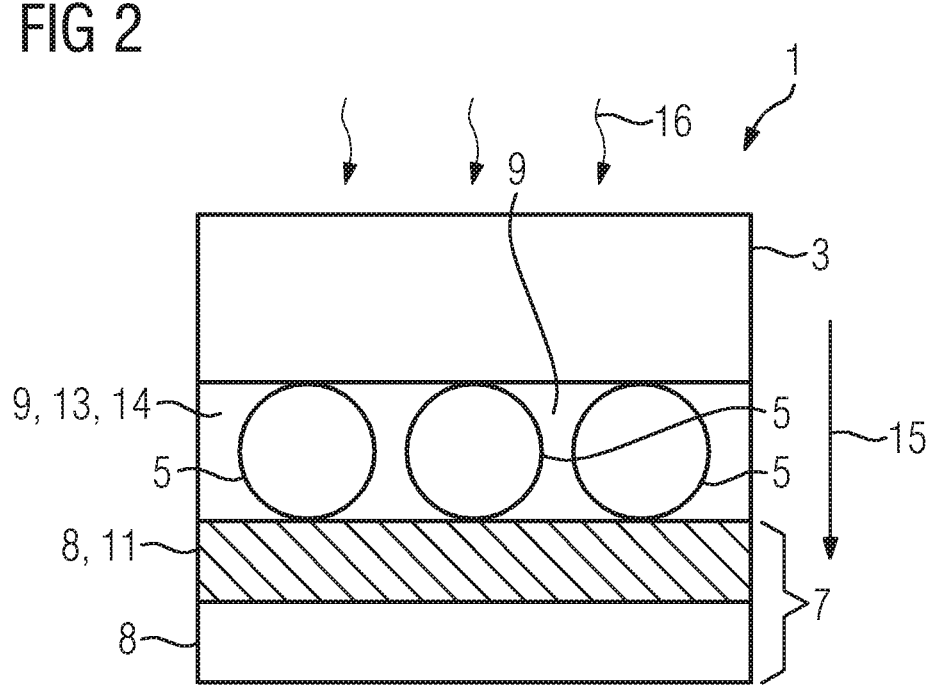
FIG. 2 schematically shows a concept of an inventive X-ray detector according to a second embodiment.

FIG. 2 shows an example embodiment of the inventive X-ray detector 1 according to a second embodiment. The X-ray detector 1 also has an underfill 13 of the interspace 9 with an underfill material. The interspace 9 has an underfill 13, comprising an underfill material 14.

Figure 3:
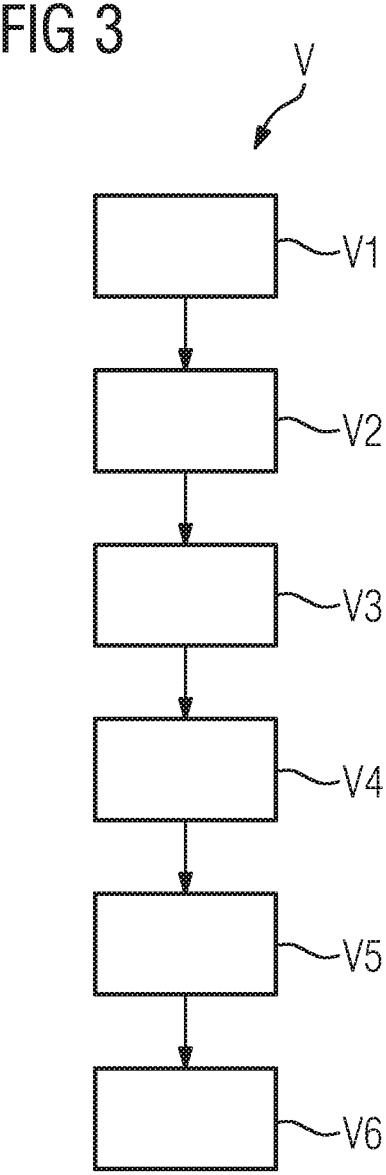
FIG. 3 schematically shows a concept of an embodiment of an inventive method for producing an embodiment of inventive X-ray detector.

FIG. 3 shows an example embodiment of the inventive method V for producing an embodiment of an inventive X-ray detector. The method comprises the following, in the following order: providing V1 the carrier unit in a panel, generating V2 the side faces along the outer circumference of the carrier unit, wherein the carrier unit remains in the panel, forming V3 the protective element on side faces of the carrier unit arranged essentially parallel to the stacking direction, wherein the protective element is formed in at least one section along the entire outer circumference and along the edges of the side faces facing the evaluation unit, separating V4 the carrier unit with the formed protective element from the panel, connecting V5 the carrier unit and the evaluation unit via a plurality of connecting elements and forming the interspace in the process, and filling V6 the interspace with an underfill material.

Figure 4:
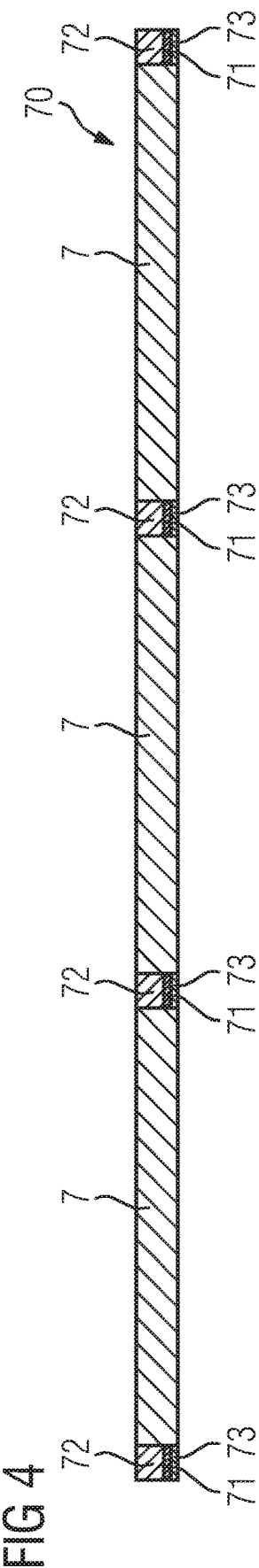
FIG. 4 schematically shows a concept of an inventive panel according to a first embodiment in a first production step.

FIG. 4 shows an example embodiment of the inventive panel 70 according to a first embodiment in a first production step. The first production step is the providing. The panel 70 comprises for example three carrier units 7. The carrier units 7 are designed separately from each other, with a stacked construction comprising connecting layer or connecting web 73, non-adhesive layer 71 and empty layers 72 being formed in each case in the intermediate region between the adjacent carrier units 7. The stacked construction comprising connecting layer or connecting web 73, non-adhesive layer 71 and empty layers 72 is also formed in the panel 70 along the outer circumference of the panel 70 around the arrangement of carrier unit 7.

During the providing, the non-adhesive layer 71 can be applied to a laminate or to the connecting layer 73. The further layers, for example empty layers 72, can then be applied to the non-adhesive layer 71.

Figure 5:
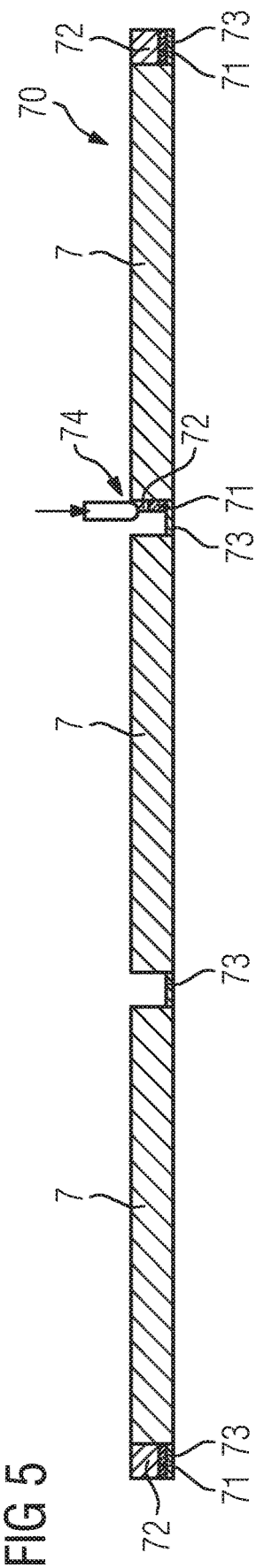
FIG. 5 schematically shows a concept of an inventive panel according to a first embodiment in a second production step.

FIG. 5 shows an example embodiment of the inventive panel according to a first embodiment in a second production step. Generating the side faces 8 includes milling along the outer circumference of the carrier unit 7. The non-adhesive layer 71 and the empty layers 72 are removed during the generating via a milling cutter 74 or by what is known as laser cutting. The empty layers 72 above the non-adhesive layer 71 are removed. The non-adhesive layer 71 can be removed. The side faces of the carrier units 7 are generated in the process. The connecting layer or the connecting web 73 is retained, so the carrier units 7 remain in the panel 70.

Figure 6:
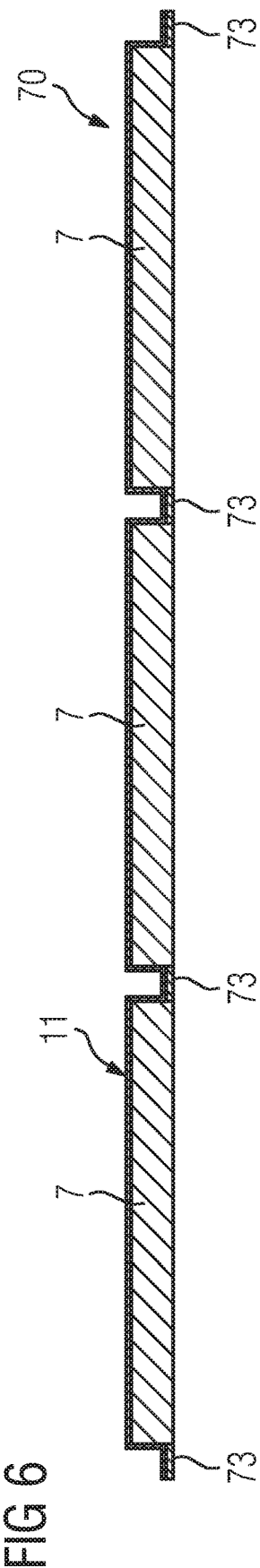
FIG. 6 schematically shows a concept of an inventive panel according to a first embodiment in a third production step.

FIG. 6 shows an example embodiment of the inventive panel according to a first embodiment in a third production step. During the forming, the protective element 11 is formed in the section of the side faces of the carrier elements 7 and on the surface facing the evaluation unit. The protective element 11 preferably has a solder resist.

FIG. 7 shows in a cross-section an example embodiment of the carrier units separated from an inventive panel according to a first embodiment. The carrier units 7 have been completely separated from the panel 70 by way of separating. The side faces 8 are now completely formed, with the protective element 11 being formed in a section. The protective element 11 formed as a coating. The protective element 11 is also formed on the surface of the carrier unit 7 facing the evaluation unit 3.

FIG. 8 shows in a side view an example embodiment of the carrier units separated from an inventive panel according to a first embodiment. The side face 8 is shown in a side view. The protective element 11 covers a section of the side face 8.

Figure 9:
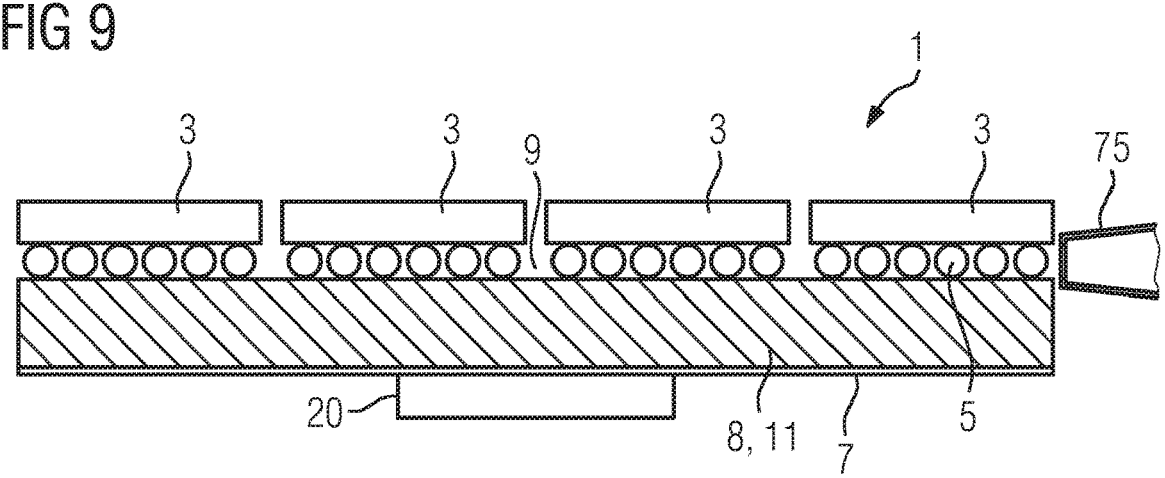
FIG. 9 schematically shows a concept of the filling according to an embodiment of the inventive method for producing an embodiment of an inventive X-ray detector at a first instant.

FIG. 9 shows an example embodiment of the filling according to an embodiment of the inventive method for producing an embodiment of an inventive X-ray detector at a first instant. The X-ray detector 1 has a carrier unit 7. By way of example, four evaluation units 3 are connected via connecting elements 5. The carrier unit 7 has the protective element 11 in one section of the side face 8. A connecting unit 20 for forwarding signals to subsequent units is formed at the surface of the carrier unit 7 remote from the evaluation unit. The pipette 75 is positioned at the interspace 9 laterally above the side face of the carrier unit 7.

Figure 10:
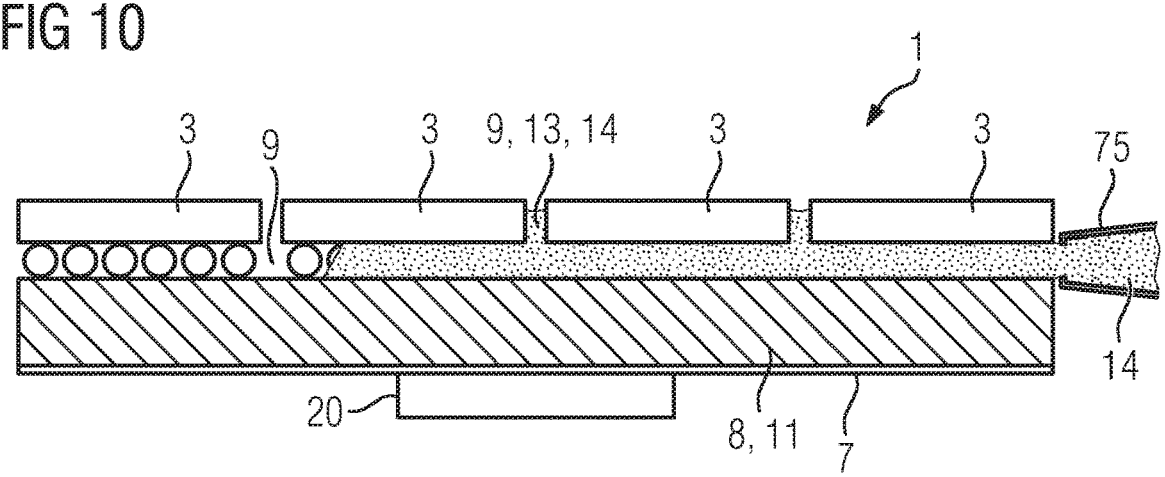
FIG. 10 schematically shows a concept of the filling according to an embodiment of the inventive method for producing an embodiment of an inventive X-ray detector at a second instant.

FIG. 10 shows an example embodiment of the filling according to an embodiment of the inventive method for producing an embodiment of an inventive X-ray detector at a second instant. The pipette 75 is filled with an underfill material 14. The underfill material 14 flows, for example by way of capillary force, into the interspace 9.

Figure 11:
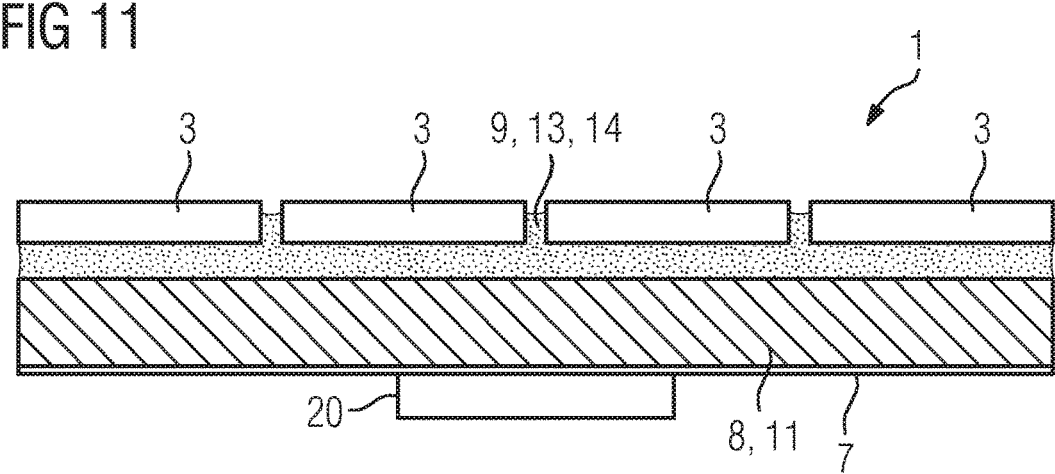
FIG. 11 schematically shows a concept of the filling according to an embodiment of the inventive method for producing an embodiment of an inventive X-ray detector at a third instant.

FIG. 11 shows an example embodiment of the filling according to an embodiment of the inventive method for producing an embodiment of an inventive X-ray detector at a third instant. The interspace 9 is completely filled with the underfill material 14. The underfill 13 is completely formed in the interspace 9. Curing or of hardening of the underfill material 14 may be included.

Figure 12:
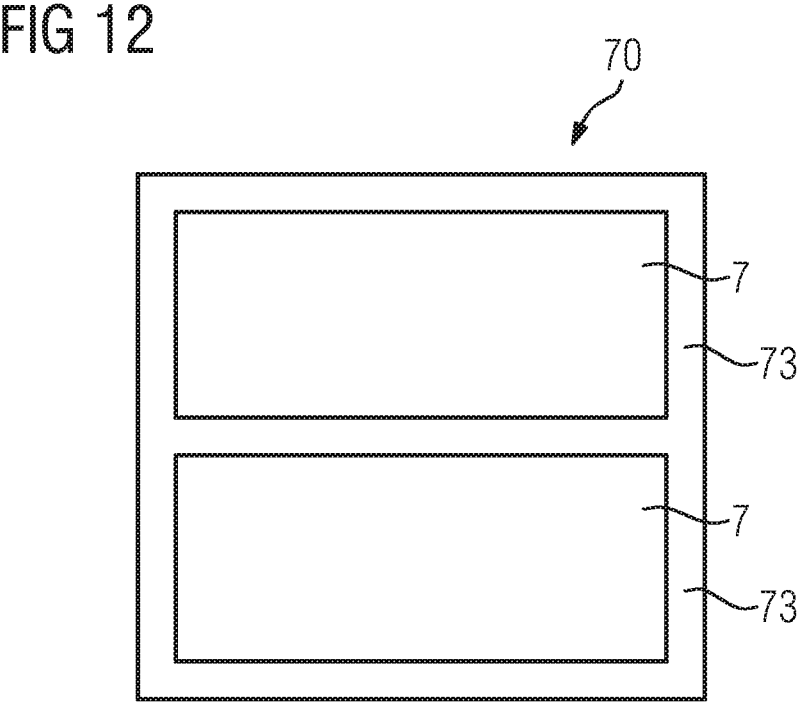
FIG. 12 schematically shows a concept of an inventive panel according to a second embodiment.

FIG. 12 shows an example embodiment of the inventive panel 70 according to a second embodiment. A plan view onto a panel 70 is shown. The panel 70 has for example two carrier units 7. A connecting layer 73 is formed around the outer circumferences of the carrier units 7.

Figure 13:
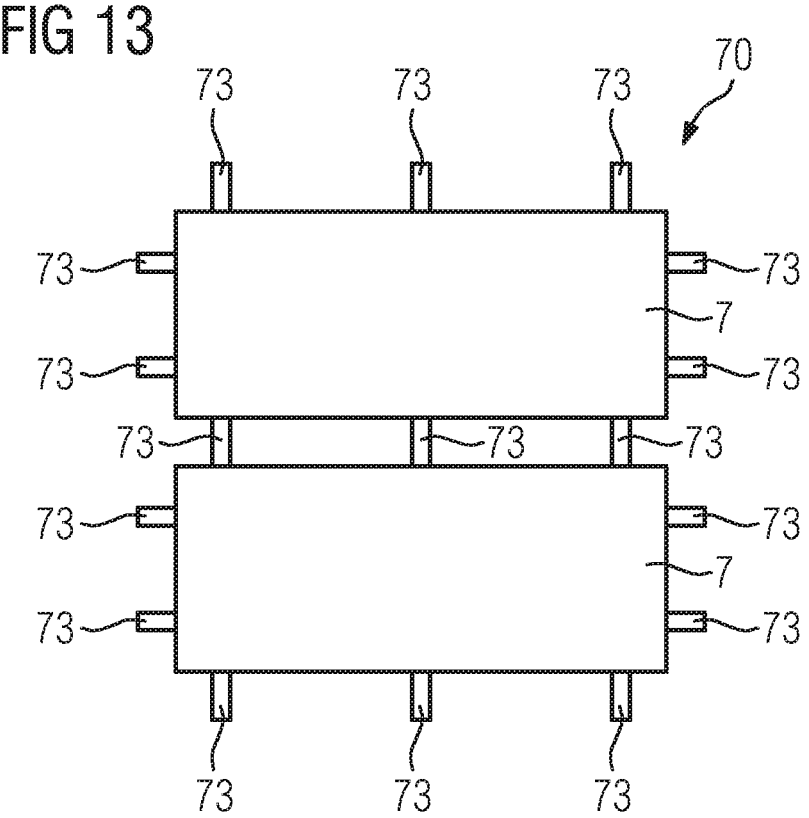
FIG. 13 schematically shows a concept of an inventive panel according to a third embodiment.

FIG. 13 shows an example embodiment of the inventive panel according to a third embodiment. A plan view onto a panel 70 is shown. The panel 70 has for example two carrier units 7. A plurality of connecting webs 73 is formed around the outer circumferences of the carrier units 7.

FIG. 14 shows an example embodiment of the inventive panel 70 according to a fourth embodiment in a first production step. The panel 70 has for example three carrier units 7. The illustration is a cross-section of the panel 70. The first production step comprises the steps of providing, of generating the side faces of the carrier unit 7 and of forming the protective element 11 on the side faces. Generating the side faces 8 comprises drilling a plurality of holes along the outer circumference of the carrier unit 7. At least partially filled holes are formed closely side by side or so as to overlap as the protective element 11 along the outer circumference of the carrier units 7. The protective element 11 is formed along the entire height of the carrier unit 7. Empty layers 72 are formed between the protective elements 11 of adjacent carrier units 7 or along the outer circumference of the panel 70 around the arrangement of carrier units 7.

FIG. 15 shows in a cross-section an example embodiment of the carrier units separated from an inventive panel 70 according to a fourth embodiment. The empty layers 72 are removed during the separating via a milling cutter 74, so the carrier units 7 are completely separated from the panel.

Figure 16:
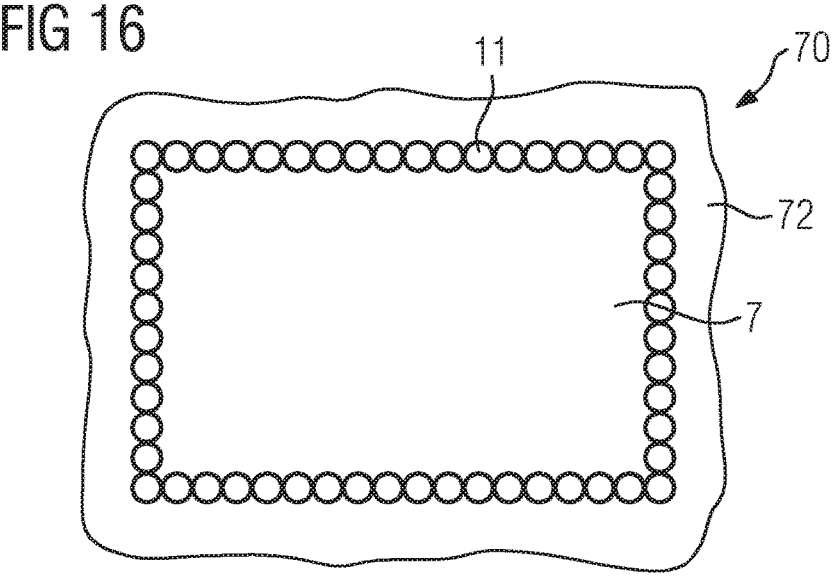
FIG. 16 schematically shows a concept of an inventive panel according to the fourth embodiment.

FIG. 16 shows an example embodiment of the inventive panel 70 according to the fourth embodiment. A plan view onto the panel 70 is shown. The protective element 11 is formed by sections of at least partially coated or partially filled mutually adjacent holes parallel to the stacking direction. Holes arranged closely side by side are formed as the protective element 11 along the outer circumference of the carrier unit 7. The region of the panel around the protective element 11 has empty layers 72.

Figure 17:
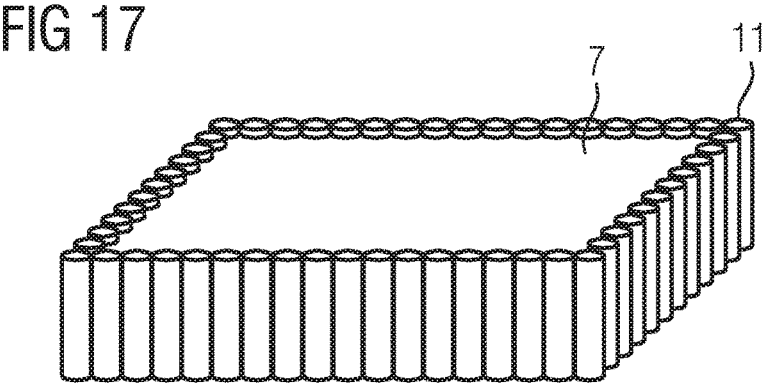
FIG. 17 schematically shows a concept of an inventive carrier unit according to the fourth embodiment in a perspective view.

FIG. 17 shows an example embodiment of the inventive carrier unit 7 according to the fourth embodiment in a perspective view. The carrier unit 7 has the protective element 11 along the outer circumference on the side faces along the entire height.

Figure 18:
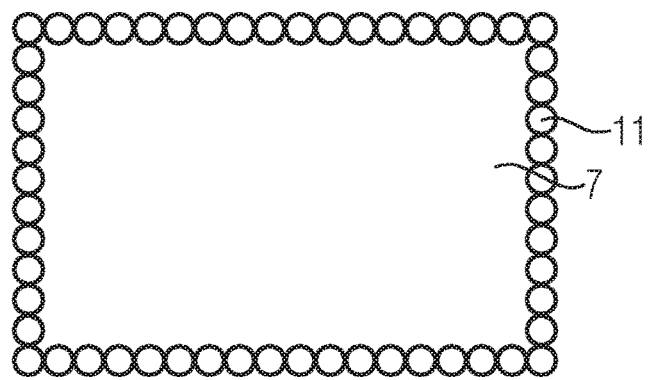
FIG. 18 schematically shows a concept of an inventive carrier unit according to the fourth embodiment in a plan view.

FIG. 18 shows in a plan view an example embodiment of the inventive carrier unit 7 according to the fourth embodiment.

Figure 19:
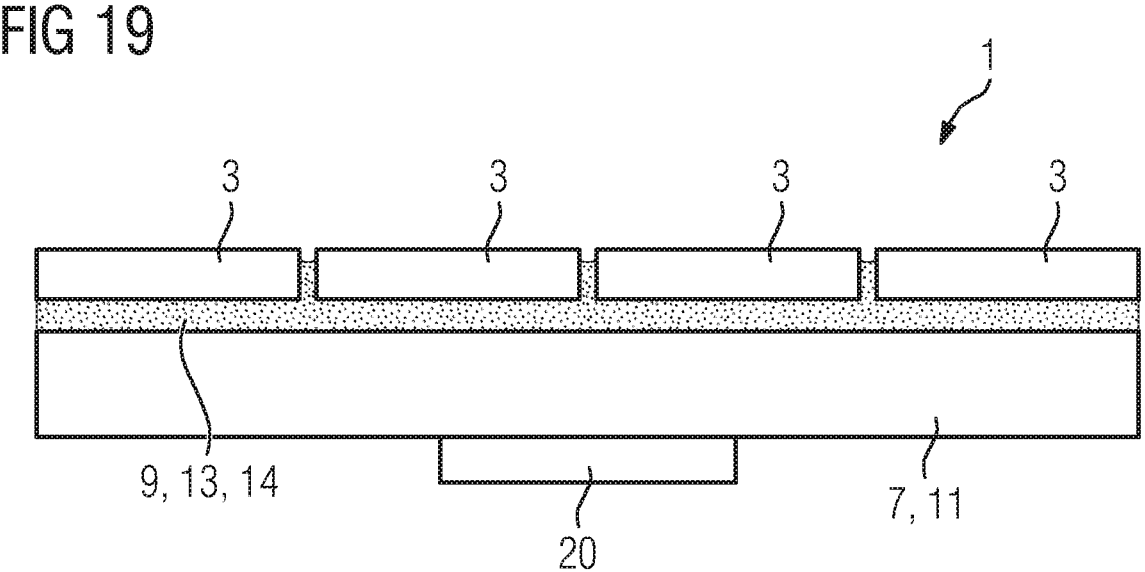
FIG. 19 schematically shows a concept of an inventive X-ray detector according to a third embodiment.

FIG. 19 shows an example embodiment of the inventive X-ray detector 1 according to a third embodiment. The X-ray detector 1 has a carrier unit 7 which comprises a protective element 11 along the entire height of the carrier unit 7. The protective element 11 can be formed by way of solder resist or holes. The underfill 13 is completely formed.

Figure 20:
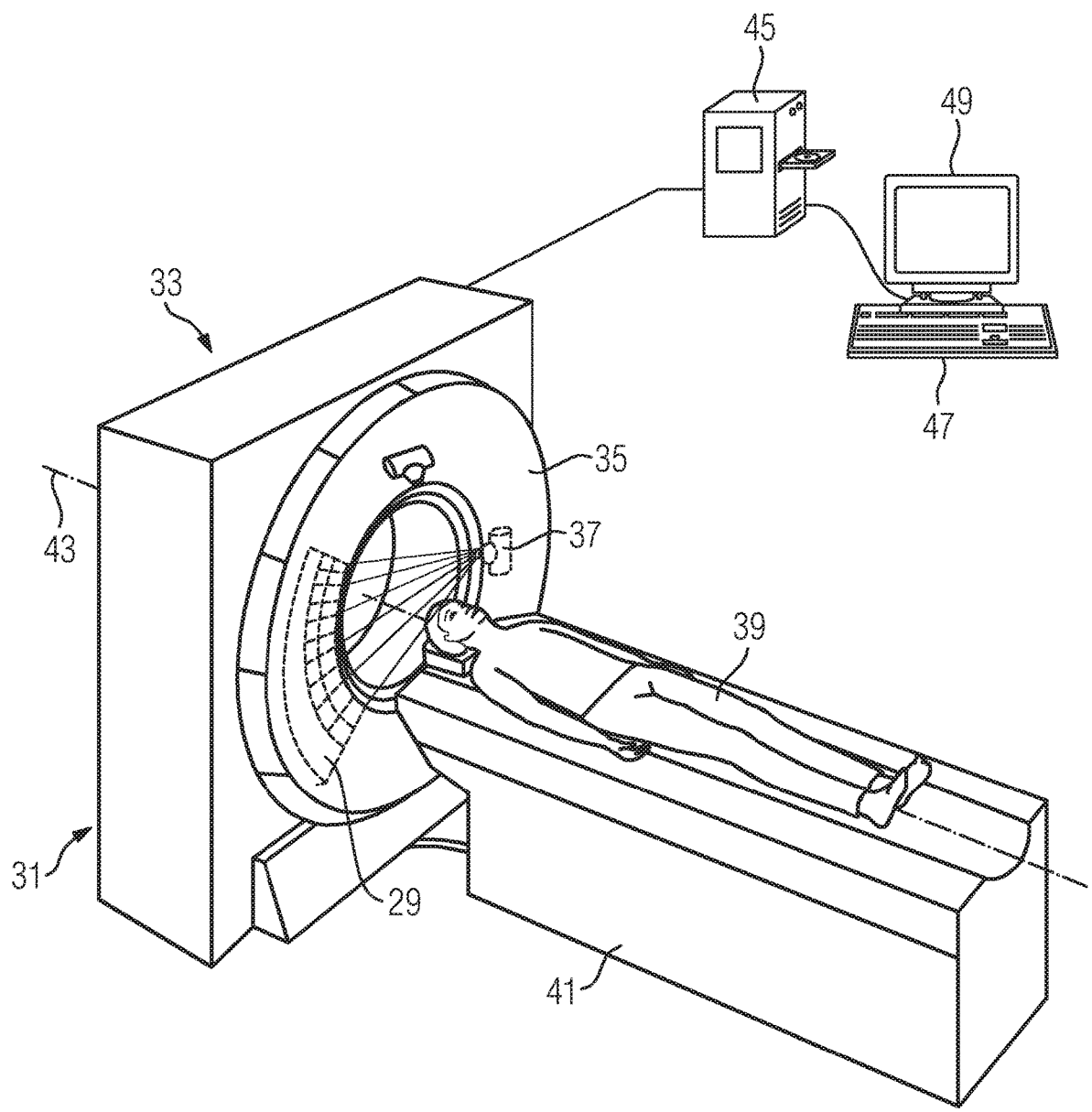
FIG. 20 schematically shows a concept of an embodiment of an inventive computerized tomography system.

FIG. 20 shows an example embodiment of the inventive computerized tomography system 31 having a detector device 29. The detector device 29 has includes an embodiment of the inventive X-ray detector. The computerized tomography system 31 includes a gantry 33 having a rotor 35. The rotor 35 comprises an X-ray source 37 and the detector device 29 having a plurality of inventive X-ray detectors of an example embodiment. The patient 39 is supported on the couch 41 and can be moved along the axis of rotation z 43 by the gantry 33. An arithmetic unit 45 is used for controlling and calculating the sectional images. An input device 47 and an output device 49 are connected to the arithmetic unit 45.

Although the invention has been illustrated in detail by the preferred example embodiment it is not limited by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector having a stacking arrangement, comprising:
   an evaluation unit; and
   a carrier unit, a protective element being formed on side faces of the carrier unit, arranged essentially parallel to a stacking direction of the stacking arrangement; and
   a plurality of connecting elements,
      the evaluation unit and the carrier unit being electrically conductively connected via the plurality of connecting elements,
      an interspace being formed between the evaluation unit, the carrier unit and the plurality of connecting elements, and
      the protective element being formed in at least one section of the side faces of the carrier unit along an entire outer circumference of the carrier unit and along edges of the side faces of the carrier unit, facing the evaluation unit, wherein the protective element extends along at least a partial height of the carrier unit beginning at an edge between the side faces and a surface of the carrier unit facing the interspace and does not extend past a surface of the carrier unit facing away from the interspace.

2. The X-ray detector of claim 1, wherein an underfill is formed in the interspace comprising an underfill material.

3. The X-ray detector of claim 2, wherein the protective element is impermeable to the underfill material.

4. The X-ray detector of claim 2, wherein the protective element is formed as a coating.

5. The X-ray detector of claim 4, wherein the protective element is also formed on a surface of the carrier unit facing the evaluation unit.

6. The X-ray detector of claim 2, wherein the protective element is formed by sections of at least partially coated or partially filled adjoining holes parallel to the stacking direction.

7. The X-ray detector of claim 1, wherein the protective element is formed as a coating.

8. The X-ray detector of claim 7, wherein the protective element is also formed on a surface of the carrier unit facing the evaluation unit.

9. The X-ray detector of claim 7, wherein the protective element is formed by sections of at least partially coated or partially filled adjoining holes parallel to the stacking direction.

10. The X-ray detector of claim 1, wherein the protective element is formed by sections of at least partially coated or partially filled adjoining holes parallel to the stacking direction.

11. The X-ray detector of claim 1, wherein the carrier unit is a multi-layer circuit board.

12. The X-ray detector of claim 1, wherein the evaluation unit includes a photodiode or an integrated circuit.

13. The X-ray detector of claim 1, wherein the plurality of connecting elements includes a plurality of solder joints.

14. A medical device comprising:
    the X-ray detector of claim 1.

15. The medical device of claim 14, wherein the medical device is a computerized tomography system.

16. The X-ray detector of claim 1, wherein the protective element is a photoresist layer.

* * * * *